United States Patent
Rad et al.

(10) Patent No.: US 12,310,616 B2
(45) Date of Patent: May 27, 2025

(54) SEPTOSTOMY BALLOON CATHETER

(71) Applicants: Elaheh Malakan Rad, Tehran (IR); Ziyad Mousa Hijazi, San Diego, CA (US)

(72) Inventors: Elaheh Malakan Rad, Tehran (IR); Ziyad Mousa Hijazi, San Diego, CA (US)

( * ) Notice: Subject to any disclaimer, the term of this patent is extended or adjusted under 35 U.S.C. 154(b) by 403 days.

(21) Appl. No.: 18/149,357

(22) Filed: Jan. 3, 2023

(65) Prior Publication Data

US 2023/0210553 A1    Jul. 6, 2023

Related U.S. Application Data

(60) Provisional application No. 63/296,104, filed on Jan. 3, 2022.

(51) Int. Cl.
*A61B 17/3205* (2006.01)
*A61B 17/00* (2006.01)

(52) U.S. Cl.
CPC ............ *A61B 17/32053* (2013.01); *A61B 2017/00557* (2013.01)

(58) Field of Classification Search
CPC .... A61B 17/32053; A61B 2017/00557; A61B 2017/22061; A61B 2017/320048; A61B 2017/00247
See application file for complete search history.

(56) References Cited

U.S. PATENT DOCUMENTS

| | | | | |
|---|---|---|---|---|
| 10,064,612 | B2 * | 9/2018 | Malakan Rad | A61L 31/022 |
| 10,524,694 | B2 * | 1/2020 | Hunter | A61B 5/0031 |
| 11,197,660 | B2 * | 12/2021 | Malakan Rad | A61B 17/0057 |
| 11,389,079 | B2 * | 7/2022 | Hunter | A61B 5/6885 |
| 11,911,141 | B2 * | 2/2024 | Hunter | A61B 5/065 |
| 2010/0042121 | A1 * | 2/2010 | Schneider | A61B 17/205 |
| | | | | 606/159 |
| 2013/0018414 | A1 * | 1/2013 | Widomski | A61B 17/1219 |
| | | | | 606/214 |
| 2014/0358180 | A1 * | 12/2014 | Malakan Rad | A61L 31/04 |
| | | | | 606/215 |
| 2017/0196478 | A1 * | 7/2017 | Hunter | A61B 5/0031 |
| 2018/0368820 | A1 * | 12/2018 | Malakan Rad | A61L 31/04 |
| 2019/0374254 | A1 * | 12/2019 | Arevalos | A61B 17/3478 |
| 2020/0245895 | A1 * | 8/2020 | Hunter | A61B 5/065 |
| 2022/0061828 | A1 * | 3/2022 | Malakan Rad | A61L 31/022 |
| 2022/0167867 | A1 * | 6/2022 | Hunter | A61B 5/065 |
| 2022/0346828 | A1 * | 11/2022 | Mathis | A61B 17/24 |
| 2023/0210553 | A1 * | 7/2023 | Rad | A61B 17/32053 |
| | | | | 606/167 |
| 2024/0298918 | A1 * | 9/2024 | Hunter | A61B 5/6885 |

* cited by examiner

*Primary Examiner* — Ryan J. Severson
(74) *Attorney, Agent, or Firm* — Charles S. Sara; Yanjun Ma; DeWitt LLP

(57) ABSTRACT

An atrio-septostomy balloon catheter device for creating an unrestrictive atrial septal defect in a thick atrial septum. The device comprises a balloon directed by an axis and a plurality of cones, wherein each of the plurality of cones has a hollow conical body, and is connected at a base thereof to a proximal side of the balloon. Preferably, the device comprises two or four cones, located equidistantly about the axis of the balloon. The plurality of cones is configured to hit the atrial septum at the same time and exert the maximal safe force on the septum for tearing it.

17 Claims, 14 Drawing Sheets

100 # SEPTOSTOMY BALLOON CATHETER

CROSS-REFERENCE TO RELATED APPLICATION

The application claims priority to U.S. Provisional Application entitled "Septostomy Balloon Catheter," Ser. No. 63/296,104, filed Jan. 3, 2022, which is incorporated herein by reference in its entirety.

FIELD OF THE INVENTION

The present disclosure is directed to a transcatheter instrument, more specifically to a balloon catheter to create an unrestrictive atrial septal defect.

BACKGROUND

Dextro-transposition (d-transposition) of great arteries is the most common cyanotic congenital heart disease in the neonatal period. FIGS. 1 and 2 illustrate a human heart with d-transposition of great arteries having a right atrium (RA), a left atrium (LA), an atrial septum (AS), a restrictive interatrial aperture (IA), a right ventricle (RV), a left ventricle (LV), an aorta (AO), and a pulmonary artery (PA). The right ventricle (RV) connects to the aorta (AO), and the left ventricle (LV) connects to the pulmonary artery (PA). The restrictive interatrial aperture (IA) can be a patent *foramen ovale* (FIG. 1) or a small atrial septal defect (FIG. 2) that prevents adequate mixing of blood between the right and left atria. In the absence of adequate inter-circulatory mixing between the right and left atria, neonatal demise is expected due to the parallel circulation. Unless specifically described otherwise, the term "aperture" refers to the restrictive interatrial communication described above, i.e., either a small patent *foramen ovale* or a small atrial septal defect.

In this anomaly, the desaturated blood of the inferior vena cava and superior vena cava drains into the right atrium, right ventricle, and aorta, whereas the saturated blood of the pulmonary veins enters the left atrium, left ventricle, and pulmonary artery. In the absence of adequate mixing between the right and left heart circulations, severe cyanosis and death ensue. Such severe cyanosis due to restrictive interatrial communication usually requires the cardiologists to perform balloon atrial septostomy for the patient to stabilize them medically prior to arterial switch operation. Atrio-septostomy balloons are devices that tear the atrial septum through a transcutaneous approach. Balloon atrial septostomy is the most frequent and the most effective urgent procedure in the neonate with transposition and poor inter-circulatory mixing, and unstable hemodynamics. This procedure may also be indicated in other congenital heart diseases such as hypoplastic left heart syndrome and restrictive interatrial communication or infants with pulmonary atresia with the intact ventricular septum. Other indications of this procedure are the presence of low cardiac output due to restrictive atrial communication in neonates with tricuspid atresia or total anomalous pulmonary venous return, in case immediate surgical intervention is not available. Finally, this procedure may be needed to decompress the left atrium in patients who are on extracorporeal membrane oxygenation.

However, in cases with a thick atrial septum, creating an adequate atrial septal defect by the commercially available atrio-septostomy balloons may not be feasible. Furthermore, the operator's attempts to exert an excessive force by forceful pull-back jerk of the balloon to overcome the thickness of the septum do not lead to success and may lead to detrimental complications.

To produce an adequate atrial septal defect in the occasions when the atrial septum is thick, there are currently five options in the armamentarium of pediatric cardiology. These include blade septostomy catheter, static balloon dilation technique, stenting of the atrial septum, wire atrial septostomy, and modified wire technique. Blade balloon atrial septostomy is not widely available, and as a result, pediatric cardiologists have less expertise and skill in performing this procedure. The small size of the left atrium can hinder this procedure. Moreover, this procedure has a higher rate of complications making a surgical backup more necessary. For instance, perforation of other cardiac structures has been reported in 3.8% of cases. Furthermore, transesophageal echocardiography is usually essential during the procedure. Atrial stenting is used for producing a long-standing communication between the atria, usually in older children. Moreover, it often needs a septal puncture using Brockenbrough needle and transesophageal echocardiography guidance. A hybrid approach is recommended to achieve a stable stent position and prevent stent embolization. Additionally, important complications may occur, including thrombus formation, embolization, and malposition of the stent with intrusion on the surrounding structures. Static balloon septostomy is not always effective in producing an adequately large communication between the atria. Furthermore, it may require a prior blade septostomy procedure. Wire and modified wire septostomy require a radiofrequency catheter for perforation of the atrial septum. In the latter, cauterization of the atrial septum and subsequent antiplatelet therapy are necessary.

Thus, there is an unmet need in the art for a device that can produce a tear in a thick atrial septum, without the need for a radiofrequency catheter and without introducing the risk of perforation of surrounding cardiac structures.

SUMMARY

Disclosed herein is an atrio-septostomy balloon catheter device 100 for tearing an atrial septum. The device 100 comprises a balloon 110 directed by an axis 111 and a plurality of cones 120, wherein each of the plurality of cones 120 has a hollow conical body, and is connected at a base thereof to a proximal side of the balloon 110.

Preferably, the plurality of cones 120 is located equidistantly about the axis 111 of the balloon 110. In some embodiments, the plurality of cones 120 numbers 2, wherein the plurality of cones 120 is located about the axis 111 of the balloon 110 at 12 and 6 o'clock. In some embodiments, the plurality of cones 120 numbers 4, wherein the plurality of cones 120 is located about the axis 111 of the balloon 110 at 12, 3, 6, and 9 o'clock. The location of the plurality of cones 120 within this disclosure is illustrative and not limiting.

The distance between the plurality of cones 120 and the axis 111 of the balloon 110 varies. In some embodiments, the plurality of cones 120 is located adjacent to the axis 111 of the balloon 110. In some embodiments, the plurality of cones 120 is located mid-way between the axis 111 and the periphery of the balloon 110. In some embodiments, the plurality of cones 120 is located at the periphery of the balloon 110.

Preferably, the plurality of cones 120 is composed of a same material as the balloon 110. Each of the plurality of cones 120 comprises a solid and filled apex to prevent it from rupture upon hitting the atrial septum and to increase its force for tearing.

In some embodiments, the base of the plurality of cones 120 is elliptical. In some embodiments, the base of the plurality of cones 120 is circular.

Preferably, the plurality of cones 120 has a vertical height 50% to 75% of the diameter of the balloon 110 along the axis 111 of the balloon.

Preferably, the base-to-apex axis of the plurality of cones 120 is parallel with the axis 111 of the balloon 110. The axis 111 of the balloon 110 has a balloon-septal contact angle with the atrial septum, and the base-to-apex axis of the plurality of cones 120 each has a conal-septal contact angle with the atrial septum, wherein the balloon-septal contact angle is equal to the conal-septal contact angle. Also preferably, the plurality of cones 120 located at an upper position has shorter slant height and vertical height than the plurality of cones 120 located at a lower position, to allow all the plurality of cones 120 to hit the atrial septum at the same time.

The objects and advantages of the disclosure will appear more fully from the following detailed description of the preferred embodiment of the disclosure made in conjunction with the accompanying drawings.

It should be understood that for clarity, not every element is necessarily labeled in every drawing. Lack of labeling should not be interpreted as a lack of disclosure.

DETAILED DESCRIPTION

The present disclosure is directed to an atrio-septostomy balloon catheter that finds application in, e.g., creating an unrestrictive atrial septal defect in neonates with a thick atrial septum and complex congenital heart disease necessitating inter-circulatory mixing between the right and left atrium.

As used herein, the "proximal" side of the balloon refers to the side that contacts the atrial septum and produces the initial tear in this structure.

Figure 1:
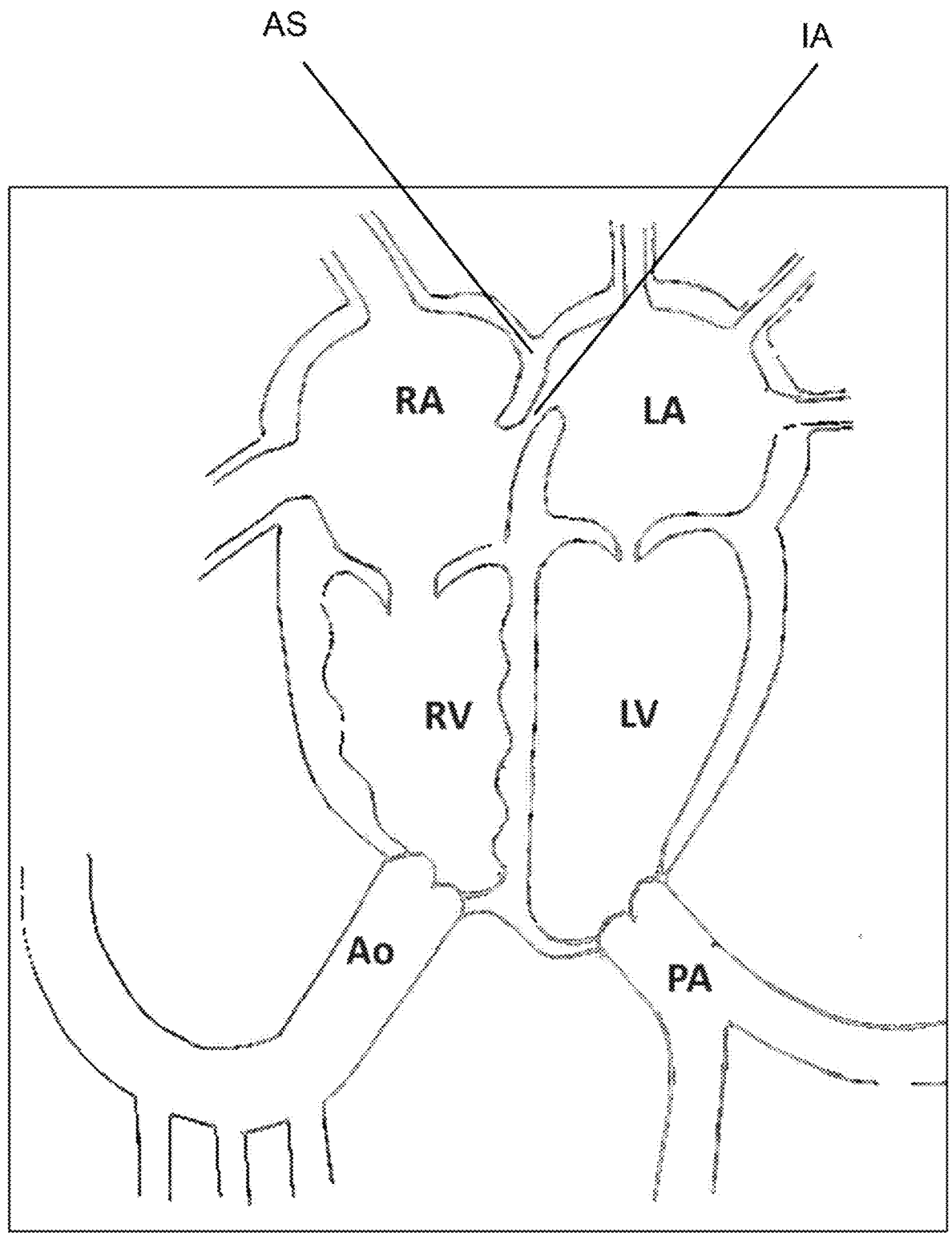
FIGS. 1 and 2 illustrate schematic representations of a human heart in a patient with dextro-transposition of great arteries with a patent *foramen ovale* (FIG. 1) and with an atrial septal defect (FIG. 2), respectively.
Figure 2:
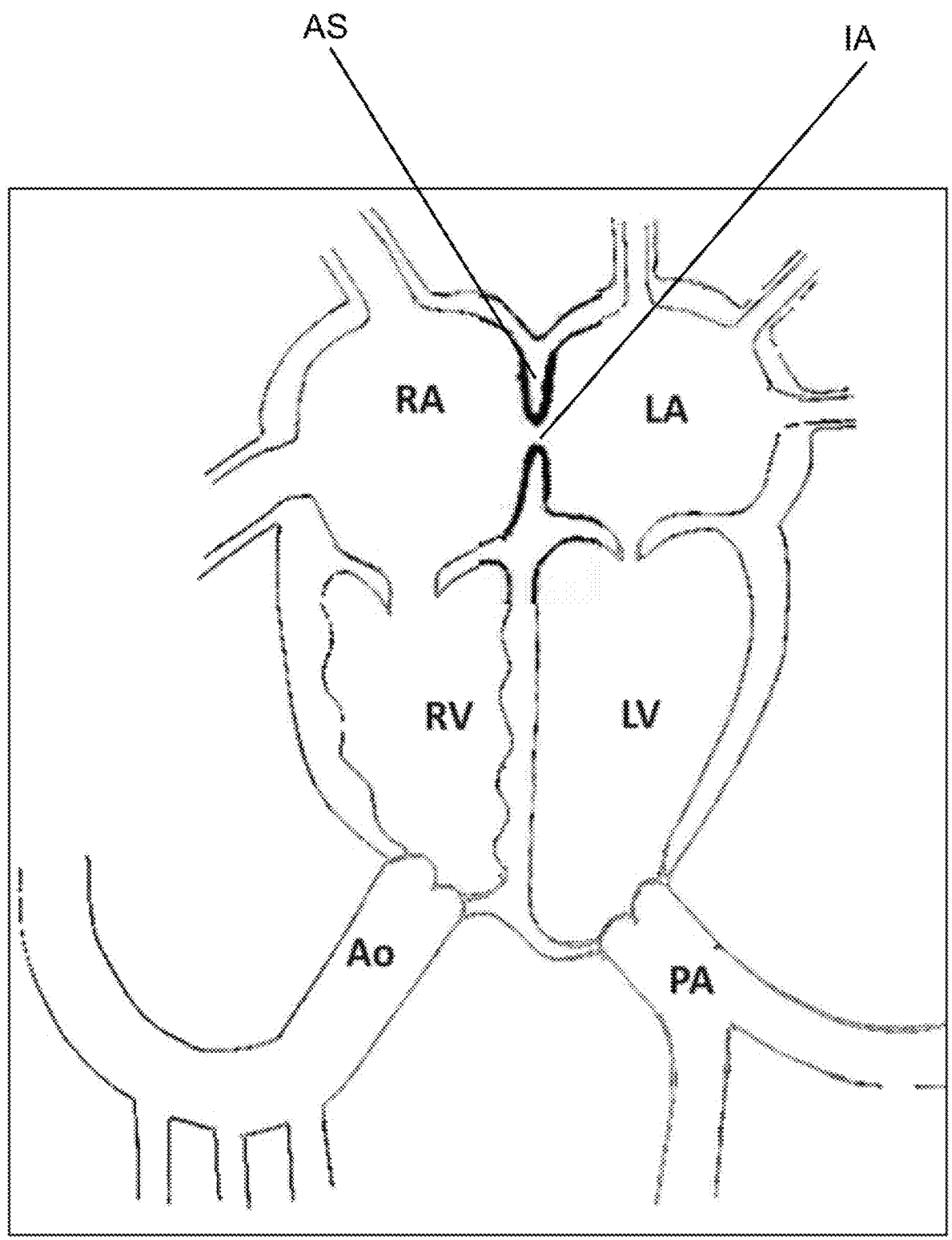
Figure 3:
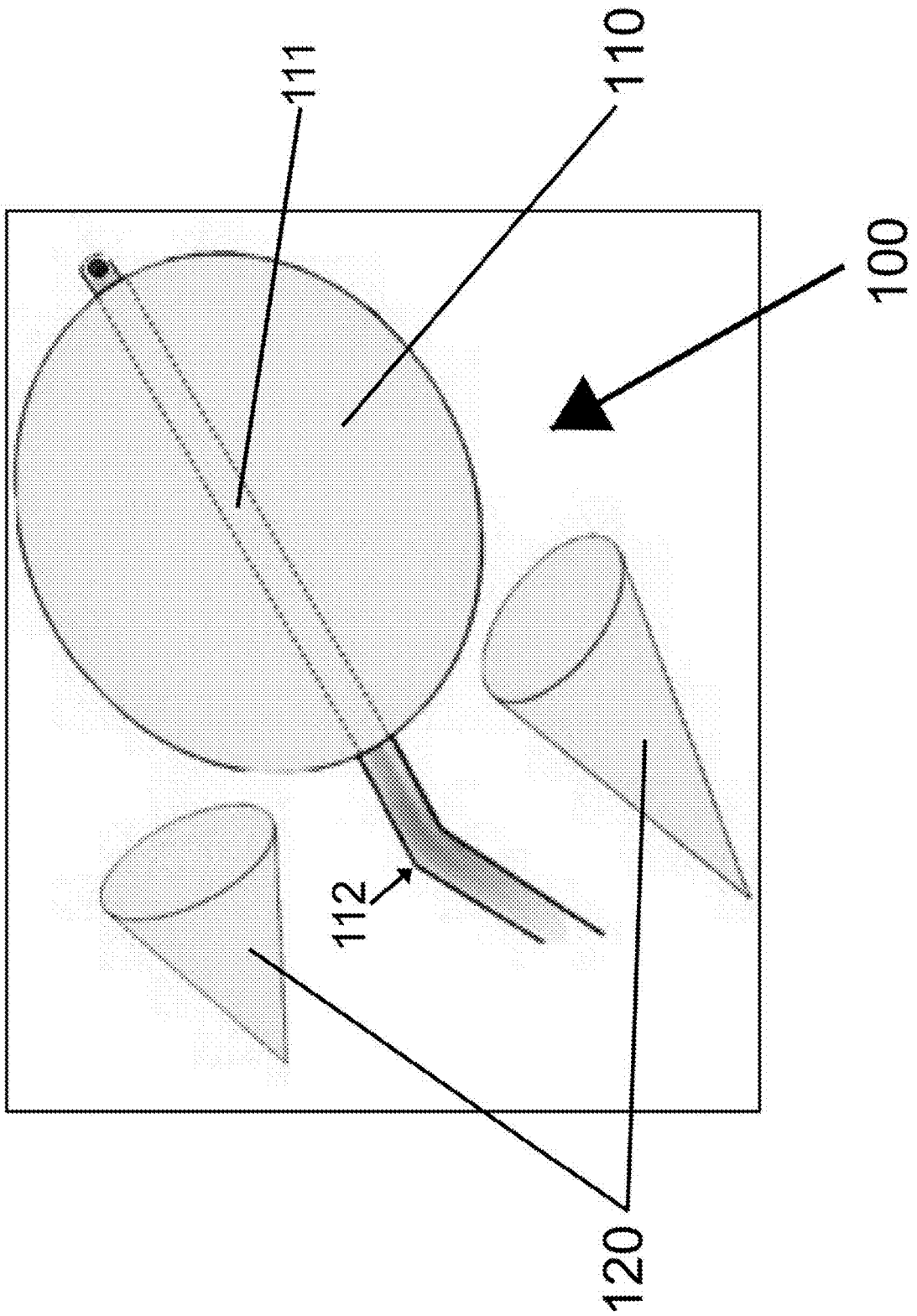
FIG. 3 shows an exploded view of an atrio-septostomy balloon catheter according to the present disclosure.

Referring to FIG. 3, disclosed herein is an atrio-septostomy balloon catheter device 100 comprising several connected parts, including an atrial septostomy balloon 110 and multiple cones 120. The balloon 110 is directed by an axis 111, and the axis 111 has an inflection point 112. The multiple cones 120 are hollow and conical-shaped appendages or outpouchings and are attached to the proximal side of the balloon 110. The atrio-septostomy balloon catheter device 100 is used for tearing the atrial septum which is thick and may otherwise require a blade atrial septostomy.

The bases of the cones 120 are attached to the proximal side of the balloon 110. The cavities of the balloon 110 and the hollow cones 120 are connected. Therefore, inflation and deflation of the cones 120 co-occur with the inflation and deflation of the balloon 110.

Figure 4:
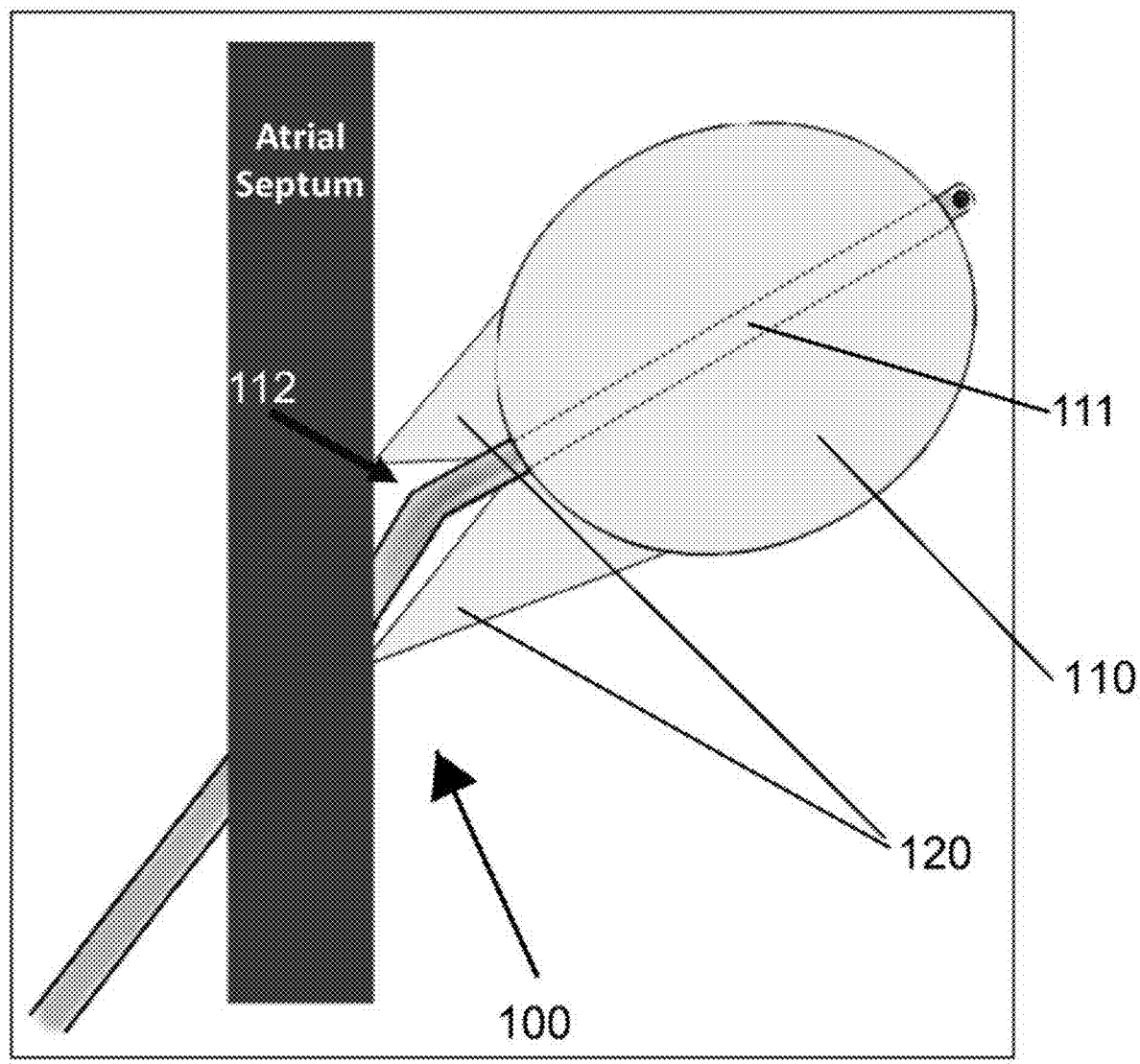
FIG. 4 illustrates an atrio-septostomy balloon catheter according to the present disclosure during the pull-back of the balloon toward the atrial septum as a quick jerk. The inflection point of the axis of the balloon is distal.
Figure 5:
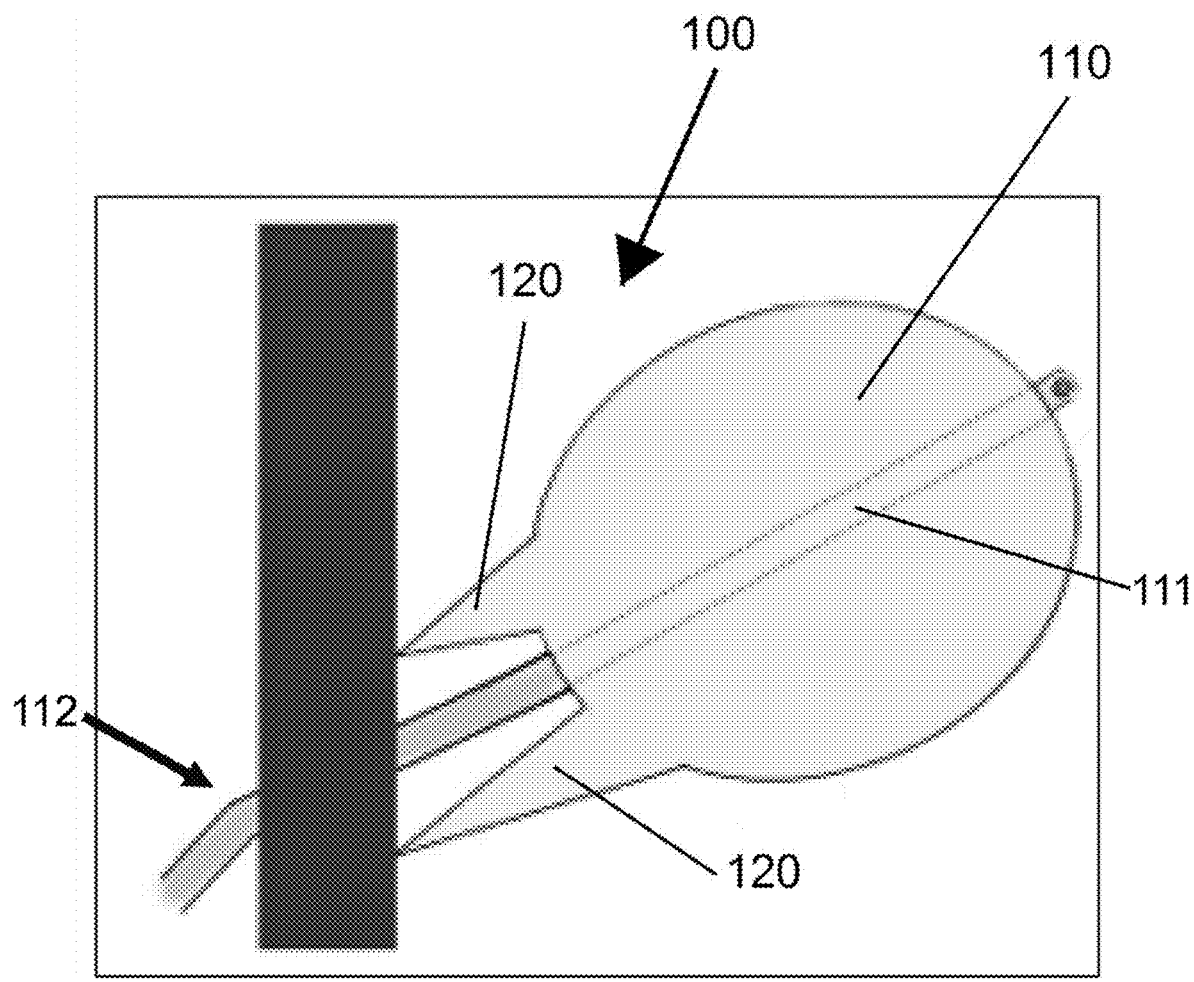
FIG. 5 illustrates an atrio-septostomy balloon catheter according to the present disclosure during the pull-back of the balloon toward the atrial septum as a rapid jerk. The inflection point of the axis of the balloon is more proximally located than that of FIG. 4.

Compared to conventional atrio-septostomy balloon catheters, the device 100 disclosed herein modifies the geometry of the proximal side of the balloon 110 that hits the septum and causes the first tearing in the septum. By changing this geometry from round to sharp, the force exerted per unit area of the atrial septum increases, facilitating septal tearing. The use of the atrio-septostomy balloon catheter device 100 is similar to conventional atrio-septostomy balloon catheters. For example, as shown in FIGS. 4-5, after insertion of the balloon catheter into the left atrium, the balloon 110 and the attached cones 120 are inflated and is then pulled back across the atrial septum by a rapid jerk. With the presence of the cones 120, the inflection point 112 of the axis 111 may be at a distal position as shown in FIG. 4, or moved to a more proximal position as shown in FIG. 5.

Figure 6:
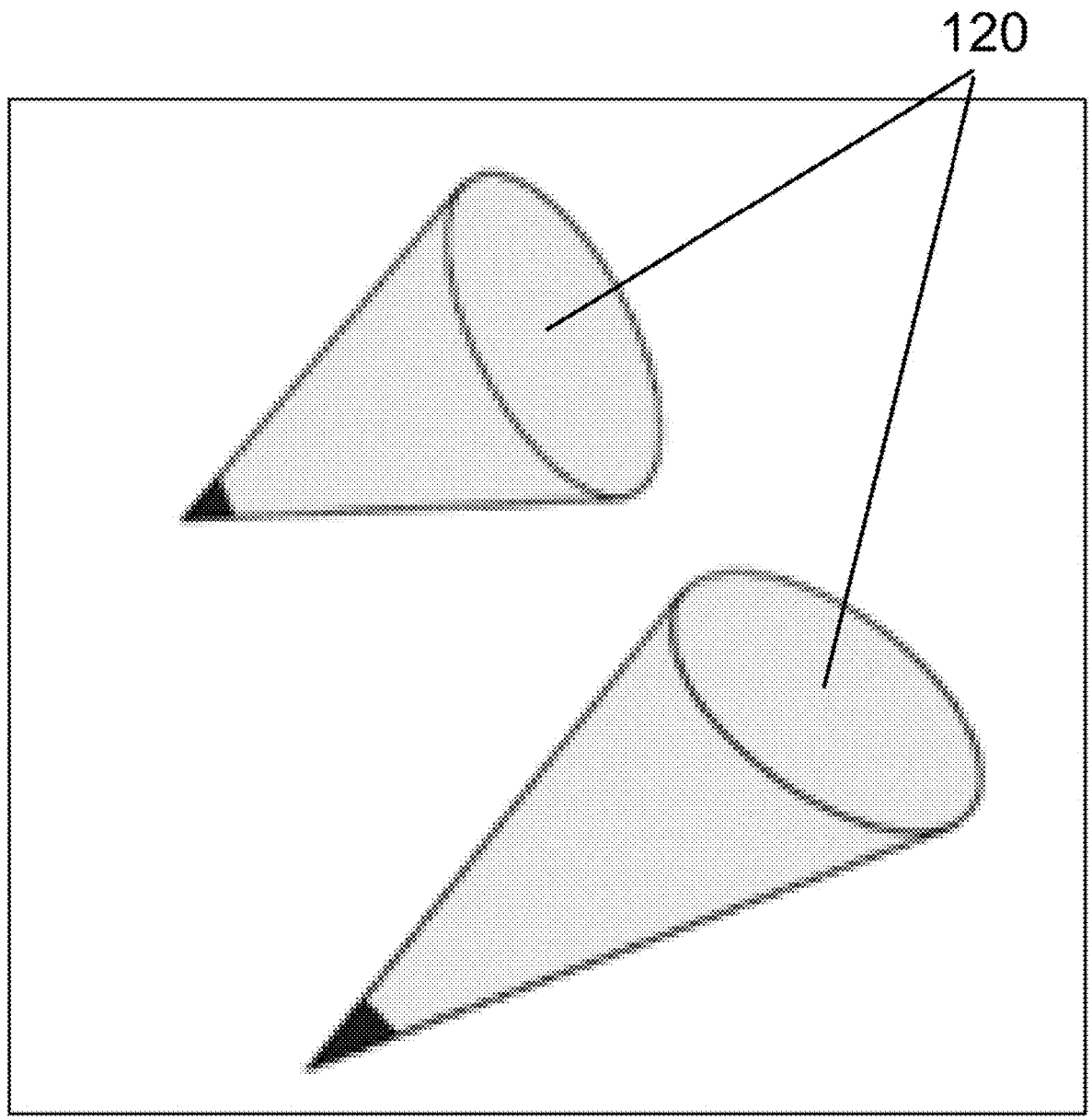
FIG. 6 illustrates the filled apex and the hollow body of the cones.

The cones 120 are composed of the same material used to make the balloon 110. However, the apices of the cones 120 are made of solid or filler material to support them from damage upon contacting the septum during rapid pull-back jerk, and the bodies have a hollow structure, similar to the balloon 110 (FIG. 6).

Figure 7:
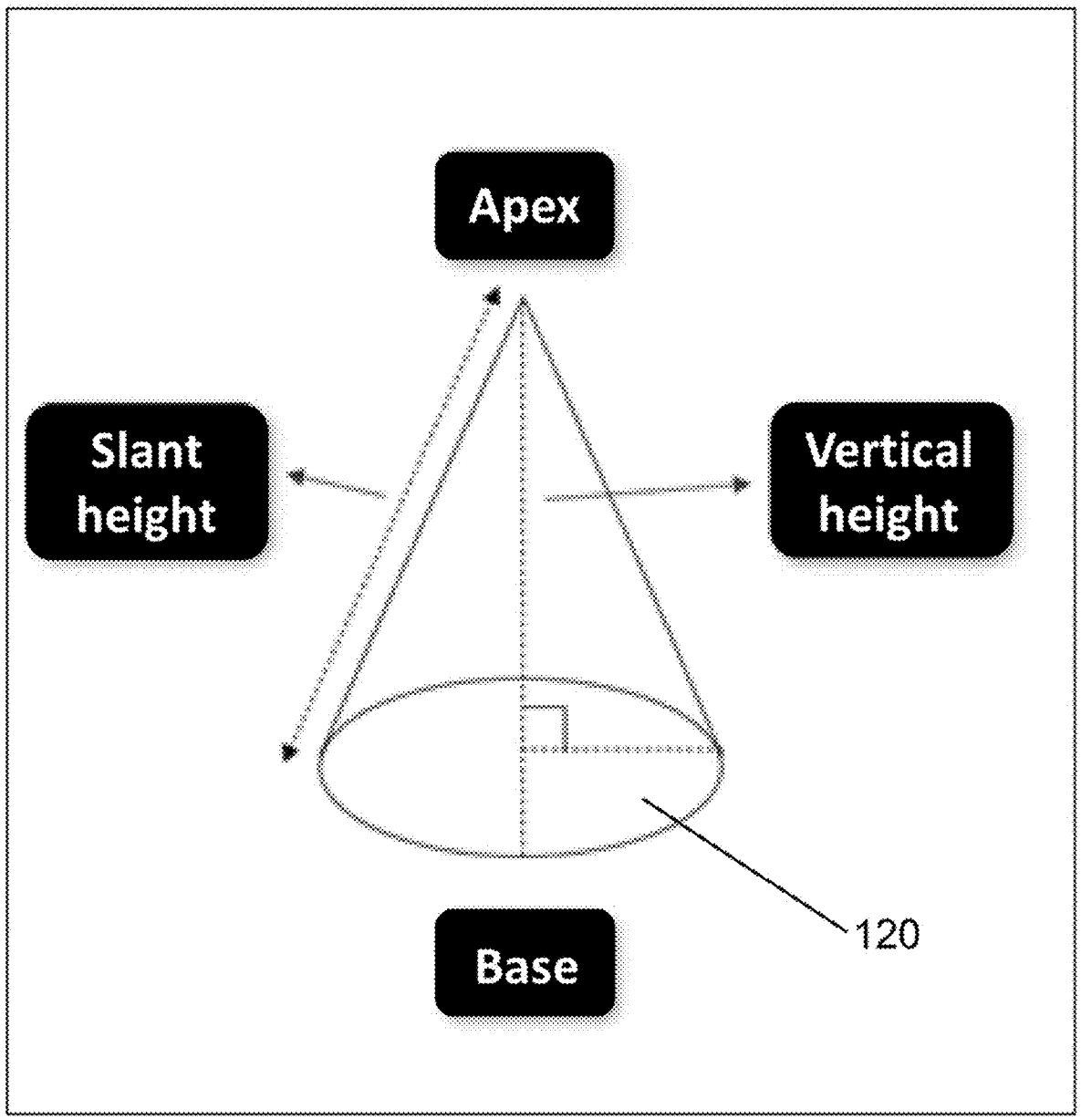
FIG. 7 illustrates the apex, base, vertical height, and slant height of a cone with an elliptical base.
Figure 8:
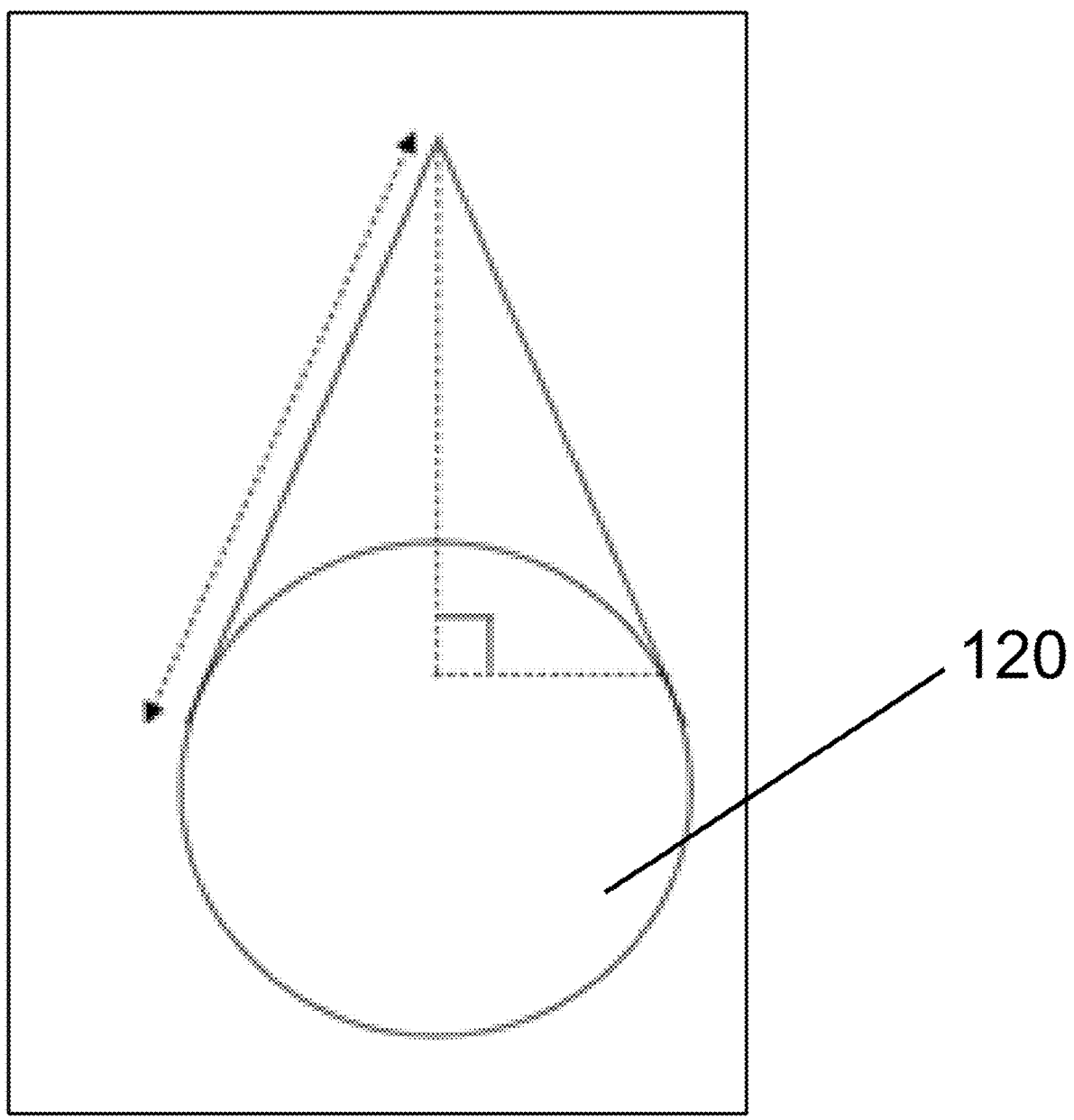
FIG. 8 shows a cone with a circular base.

The base of the cones 120 may be elliptical or circular, as illustrated by FIG. 7 (elliptical) and FIG. 8 (circular). The vertical height of the cones 120 is about 50% to 75% of the diameter of the balloon 110 along the axis 111. A shorted vertical height may make the tearing ineffective, and a longer vertical height may increase the risk of damage to the surrounding structures, particularly in the setting of a small left atrium.

Figure 9:
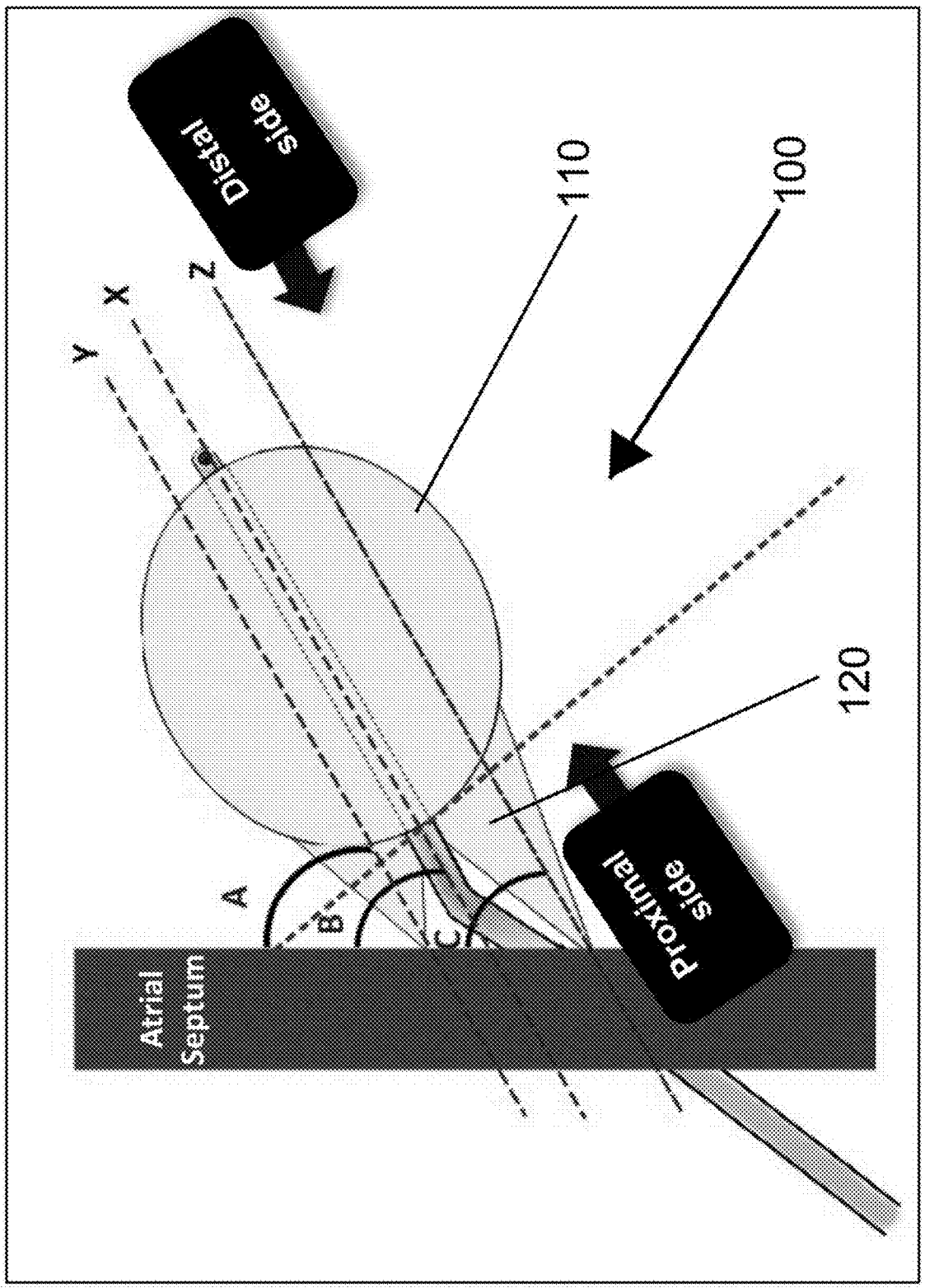
FIG. 9 shows a schematic representation of an atrio-septostomy balloon catheter according to the present disclosure, wherein the base-to-apex axes (dashed lines "Y" and "Z") of the cones are parallel with the axis of the balloon (dashed line "X"), and the balloon-septal angle (angle "B") and the conal-septal angles (angles "A" and "C") are equal.

As shown in FIG. 9, the base-to-apex axes of the cones 120 (indicated by dashed lines "Y" and "Z") are parallel with the axis 111 of the balloon 110 (indicated by dashed line "X"). The angle between the axis 111 of the balloon 110 and the atrial septum is referred to as balloon-septal contact angle (indicated by angle "B"). The angles between the base-to-apex axes of the cones 120 and the atrial septum are referred to as conal-septal contact angles (indicated by angles "A" and "C"). To exert the maximal safe force on the septum to tear it, the balloon-septal contact angle and the conal-septal contact angles are equal. The parallel axes and equal angles of the assembly components are used to concentrate the force on the area of interest to produce the appropriate opening. Due to the contact angles, the slant height and vertical height of the upper cone is smaller than the slant height and vertical height of the lower cone. The differential sizes allow both cones to hit the atrial septum at the same time, such that a more significant force is exerted on the septum for tearing the septum to an adequate size.

Figure 10:
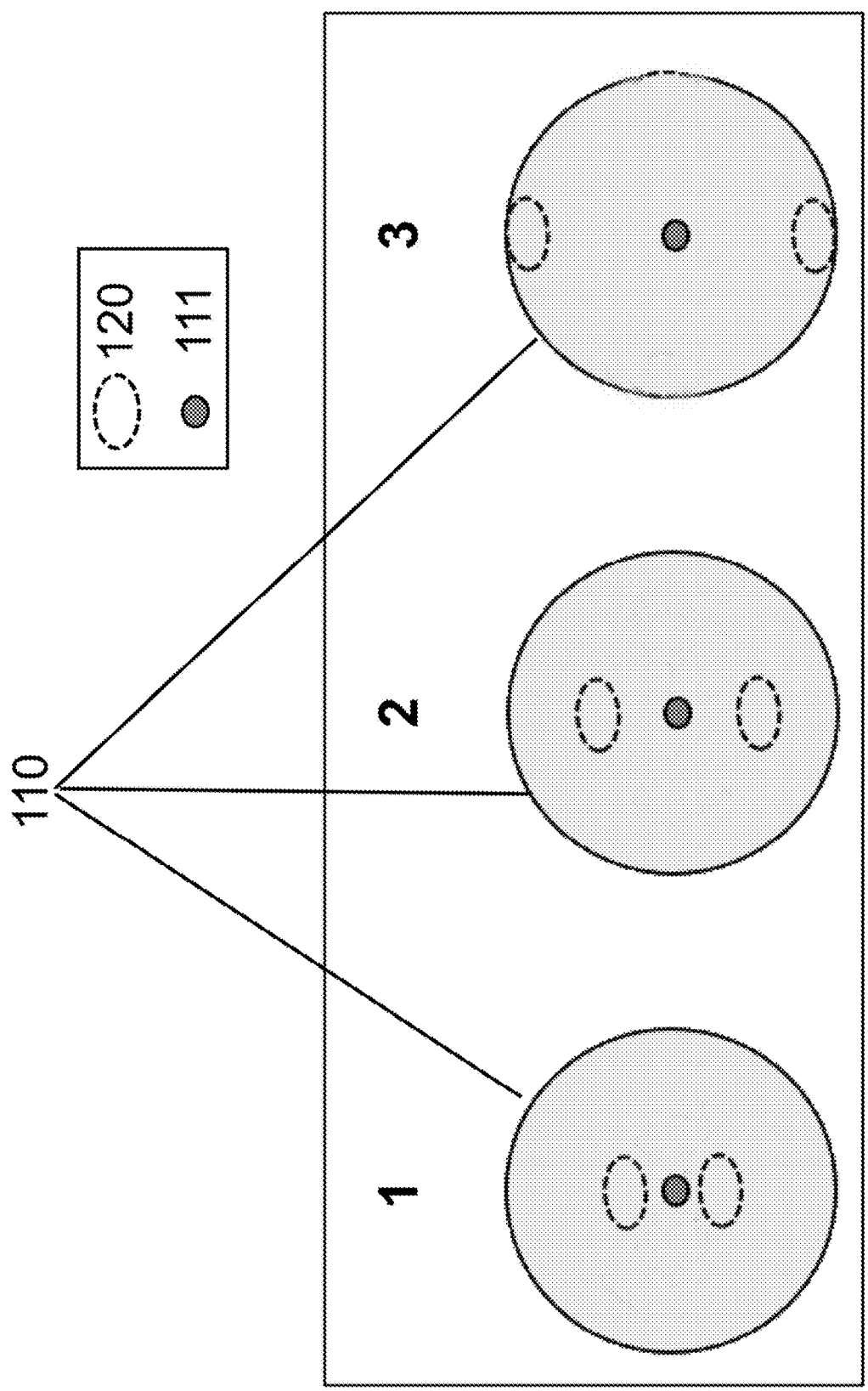
FIG. 10 shows top plan views of the atrio-septostomy balloon catheter according to the present disclosure comprising two cones, wherein the cones are located: (1) adjacent to the axis of the balloon; (2) mid-way between the axis and the periphery of the balloon; and (3) at the periphery of the balloon.
Figure 11:
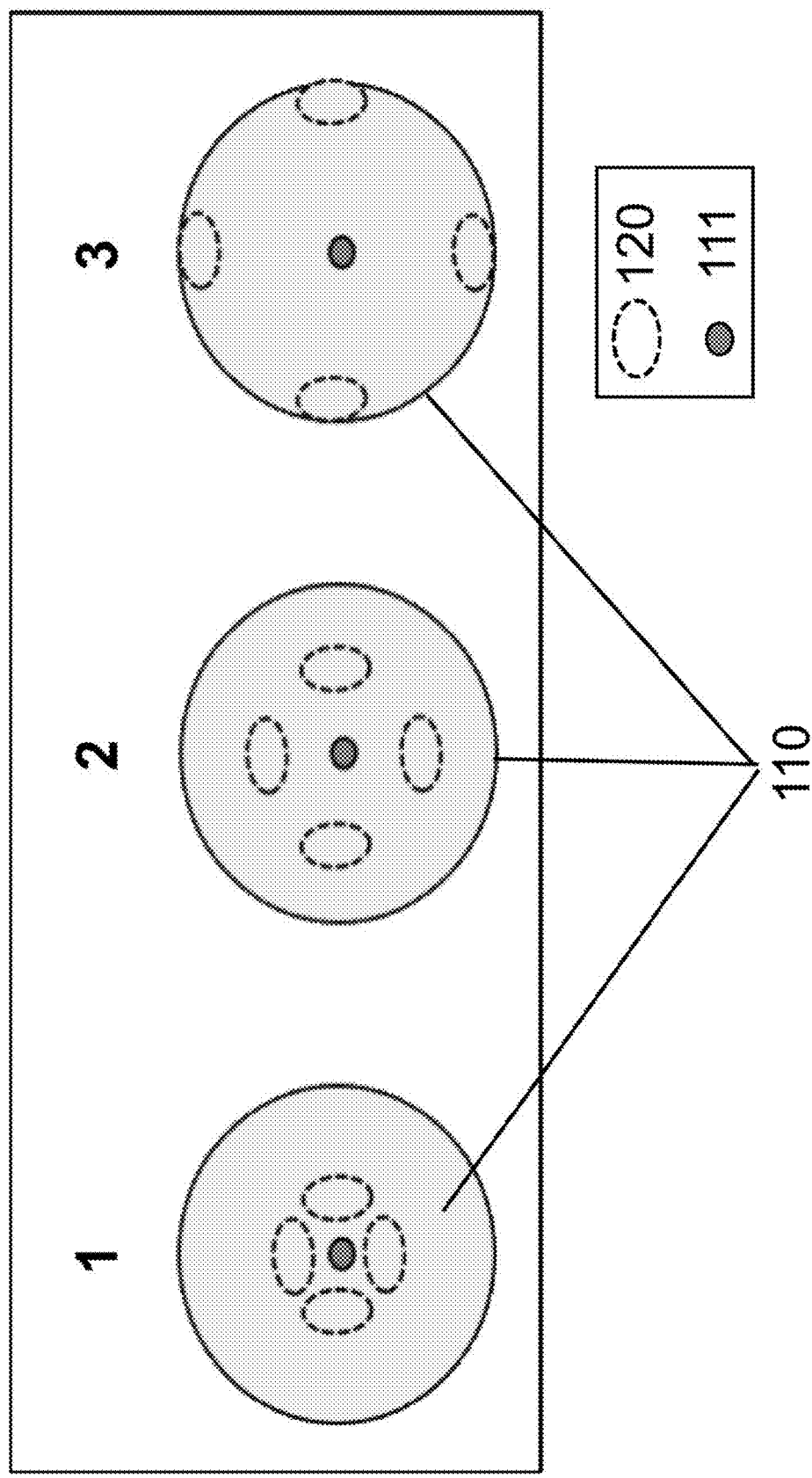
FIG. 11 shows top plan views of the atrio-septostomy balloon catheter according to the present disclosure comprising four cones, wherein the cones are located: (1) adjacent to the axis of the balloon; (2) mid-way between the axis and the periphery of the balloon; and (3) at the periphery of the balloon.

Preferably, the atrio-septostomy balloon catheter device 100 comprises two or four cones 120, as shown in FIGS. 10 and 11. The number of the cones 120 (two versus four) depends on the thickness of the atrial septum that is supposed to be torn by this atrio-septostomy balloon catheter device 100. Four cones are considered for thicker septa and two for less thick septa. For example, a two-cone balloon device 100 is used for atrial septa with mild to moderate thickness, and a four-cone balloon device 100 is used for moderate to severe thickness. The cones 120 are placed equidistantly about the axis 111 of the balloon 110. By way of non-limiting example, the cones 120 may be placed at 12 and 6 o'clock in the two-cone embodiment (FIG. 10) or 12, 3, 6, and 9 o'clock in the four-cone embodiment (FIG. 11). Any reference to these specific positions within this disclosure should be assumed to be illustrative and not limiting. By way of further non-limiting example, the cones 120 may be placed at 1 and 7 o'clock in the two-cone embodiment or 2, 5, 8, and 11 o'clock in the four-cone embodiment.

As shown in FIGS. 10 and 11, the distance of the cones 120 from the axis 111 of the balloon 110 may vary in three embodiments: (1) adjacent to the axis 111 of the balloon 110; (2) mid-way between the axis 111 and the periphery of the balloon 110; and (3) at the periphery of the balloon 110. The configuration having more adjacent distance between the cones 120 and the axis 111 is used for smaller orifices and the configuration having farther distance between the cones 120 and the axis 111 is for larger ones. In all three embodiments, the peripheral diameter (outer-to-outer diameter) of the cones 120 does not exceed the peripheral diameter of the balloon 110 (FIGS. 10 and 11). As used herein, the "periphery" of the balloon 110 refers to the maximum boundary of the balloon at the direction perpendicular to the axis 111. The "peripheral diameter" of the balloon 110 refers to the diameter of the balloon that is perpendicular to the axis 111.

Figure 12:
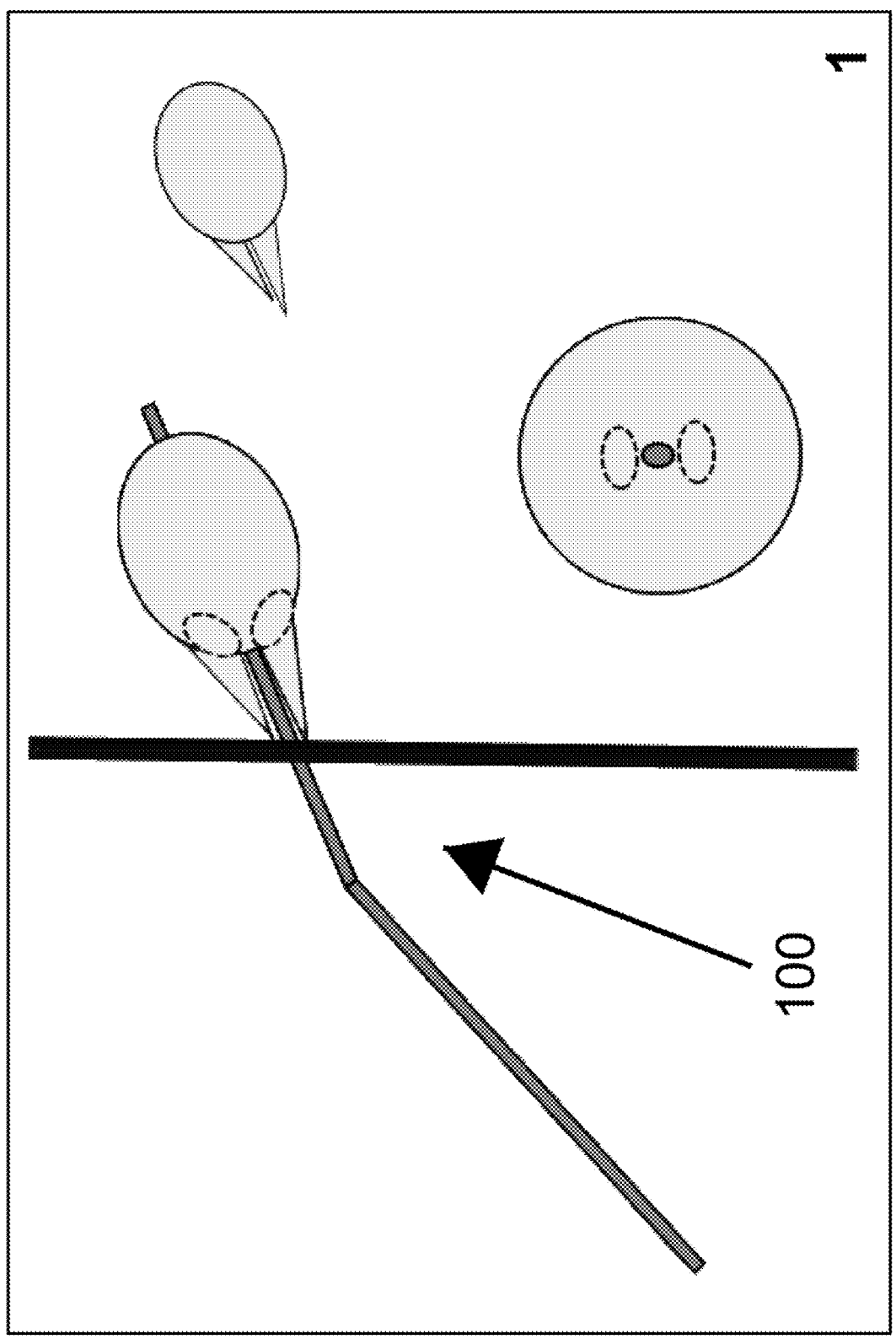
FIG. 12 illustrates an embodiment of the atrio-septostomy balloon catheter according to the present disclosure comprising two cones, wherein the two cones are placed adjacent to the axis of the balloon at 12 and 6 o'clock. The cone placed at 12 o'clock has shorter slant height and vertical height than the cone attached at 6 o'clock. The outer-to-outer diameter of the two cones does not exceed the peripheral diameter of the balloon.
Figure 13:
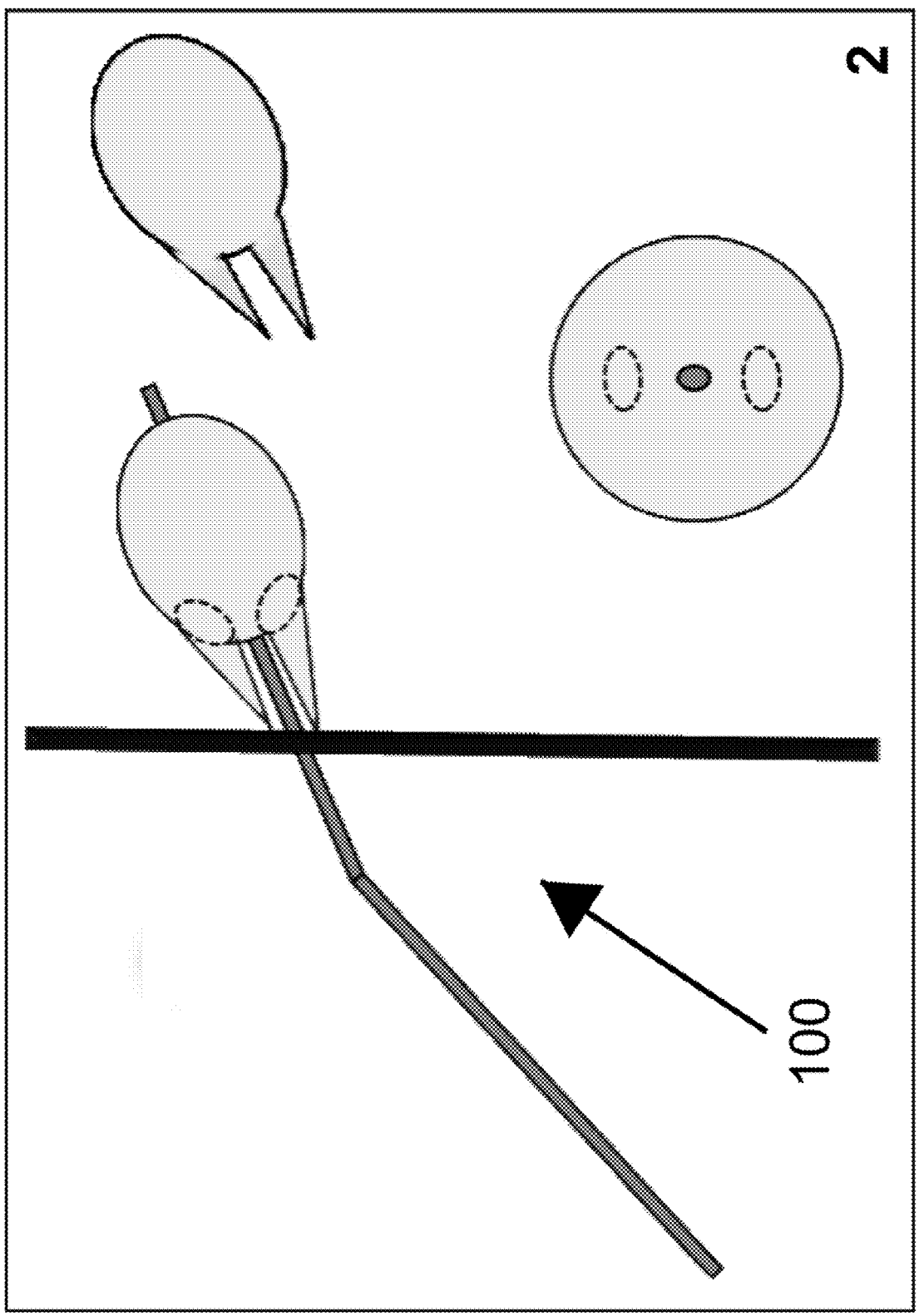
FIG. 13 illustrates another embodiment of the atrio-septostomy balloon catheter according to the present disclosure comprising two cones, wherein the two cones are placed mid-way between the axis and the periphery of the balloon at 12 and 6 o'clock. The cone placed at 12 o'clock has shorter slant height and vertical height than the cone attached at 6 o'clock. The outer-to-outer diameter of the two cones does not exceed the peripheral diameter of the balloon.
Figure 14:
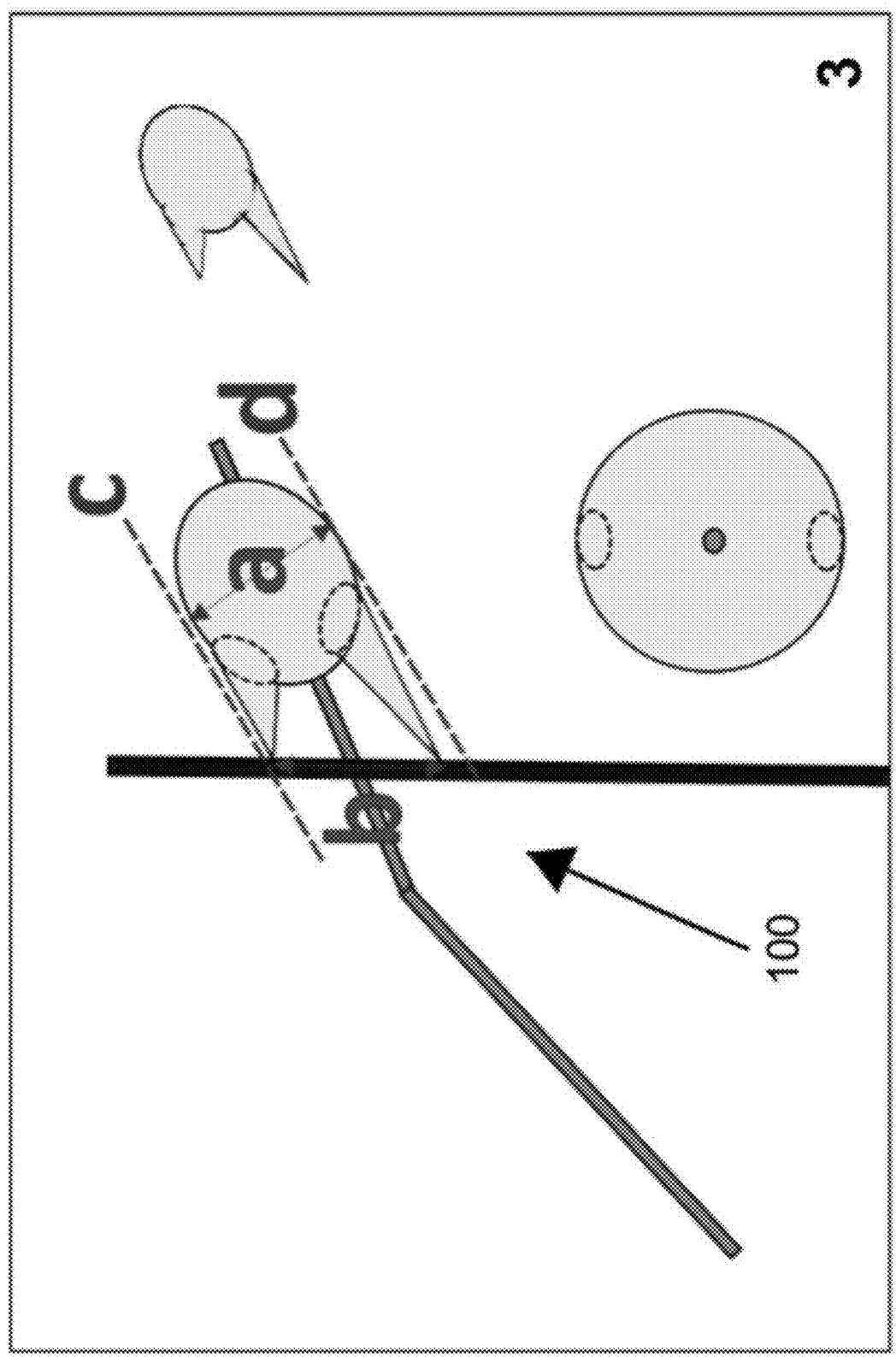
FIG. 14 illustrates another embodiment of the atrio-septostomy balloon catheter according to the present disclosure comprising two cones, wherein the two cones are placed at the periphery of the balloon at 12 and 6 o'clock. The cone placed at 12 o'clock has shorter slant height and vertical height than the cone attached at 6 o'clock. The outer-to-outer diameter of the two cones (indicated by the distance between dashed lines "c" and "d") does not exceed the peripheral diameter of the balloon ("a").

Using the atrio-septostomy balloon catheter device 100 comprising two cones 120 as an example, FIGS. 12-14 shows the three different distances of the cones 120 from the axis 111. In each of the three embodiments, the cone placed at 12 o'clock has shorter slant height and vertical height than the cone attached at 6 o'clock. As specifically shown in FIG. 14, the outer-to-outer diameter of the two cones (indicated by the distance between the dashed lines "c" and "d") does not exceed the peripheral diameter (indicated by "a") of the balloon.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations and systems described herein may be used alone or in combination with other configurations and systems. It is to be expected that various equivalents, alternatives and modifications are possible within the scope of the foregoing description.

Any version of any component of the disclosure may be used with any other component of the disclosure. The elements described herein can be used in any combination whether explicitly described or not.

As used herein, the singular forms "a," "an," and "the" include plural referents unless the content clearly dictates otherwise.

As used herein, the term "or" is an inclusive "or" operator and is equivalent to the term "and/or" unless the context clearly dictates otherwise.

As used herein, the term "about" refers to ±10% of the variable referenced.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

The systems of the present disclosure can comprise, consist of, or consist essentially of the essential elements and limitations described herein, as well as any additional or optional components, or limitations described herein or otherwise useful in the art. The disclosure provided herein suitably may be practiced in the absence of any element which is not specifically disclosed herein.

While this disclosure may be embodied in many forms, what is described in detail herein is a specific preferred embodiment of the disclosure. The present disclosure is an exemplification of the principles of the disclosure is not intended to limit the disclosure to the particular embodiments illustrated. It is to be understood that this disclosure is not limited to the particular examples, configurations, and materials disclosed herein as such configurations and materials may vary somewhat. It is also understood that the terminology used herein is used for the purpose of describing particular embodiments only and is not intended to be limiting since the scope of the present disclosure will be limited to only the appended claims and equivalents thereof.

What is claimed is:

1. An atrio-septostomy balloon catheter device for tearing an atrial septum, comprising:

a balloon directed by an axis; and a plurality of cones, wherein each of the plurality of cones has a hollow conical body, and is connected at a base thereof to a proximal side of the balloon.

2. The device of claim 1, wherein the plurality of cones is located equidistantly about the axis of the balloon.

3. The device of claim 1, wherein the plurality of cones numbers 2.

4. The device of claim 3, wherein the plurality of cones is located about the axis of the balloon at 12 and 6 o'clock.

5. The device of claim 1, wherein the plurality of cones numbers 4.

6. The device of claim 5, wherein the plurality of cones is located about the axis of the balloon at 12, 3, 6, and 9 o'clock.

7. The device of claim 1, wherein the plurality of cones is located adjacent to the axis of the balloon.

8. The device of claim 1, wherein the plurality of cones is located mid-way between the axis and the periphery of the balloon.

9. The device of claim 1, wherein the plurality of cones is located at the periphery of the balloon.

10. The device of claim 1, wherein the plurality of cones is composed of a same material as the balloon.

11. The device of claim 1, wherein each of the plurality of cones comprises a solid and filled apex to prevent it from rupture upon hitting the atrial septum and to increase its force for tearing.

12. The device of claim 1, wherein the base of the plurality of cones is elliptical.

13. The device of claim 1, wherein the base of the plurality of cones is circular.

14. The device of claim 1, wherein the plurality of cones has a vertical height 50% to 75% of the diameter of the balloon along the axis of the balloon.

15. The device of claim 1, wherein the base-to-apex axis of the plurality of cones is parallel with the axis of the balloon.

16. The device of claim 1, wherein the axis of the balloon has a balloon-septal contact angle with the atrial septum, and the base-to-apex axis of the plurality of cones each has a conal-septal contact angle with the atrial septum, wherein the balloon-septal contact angle is equal to the conal-septal contact angle.

17. The device of claim 1, wherein the plurality of cones located at an upper position has shorter slant height and vertical height than the plurality of cones located at a lower position, to allow all the plurality of cones to hit the atrial septum at the same time.

* * * * *